United States Patent [19]

Poser et al.

[11] Patent Number: 5,371,191
[45] Date of Patent: Dec. 6, 1994

[54] OSTEOINDUCTIVE PROTEIN MIXTURES AND PURIFICATION PROCESSES

[76] Inventors: James W. Poser, 12180 W. 18th Dr., Lakewood, Colo. 80215; James J. Benedict, 13206 W. 33rd Pl., Golden, Colo. 80401

[21] Appl. No.: 142,686

[22] Filed: Oct. 26, 1993

Related U.S. Application Data

[62] Division of Ser. No. 689,459, Apr. 22, 1991, Pat. No. 5,290,763.

[51] Int. Cl.$^5$ .......................... C07K 3/02; C07K 3/20; C07K 3/26; C07K 15/06
[52] U.S. Cl. ...................... 530/350; 530/399; 530/414; 530/416; 530/417; 530/840
[58] Field of Search ................. 424/549; 514/2, 12, 514/21; 530/350, 355, 399, 412, 414, 840, 416, 417, 422, 423

[56] References Cited

U.S. PATENT DOCUMENTS

| | | | |
|---|---|---|---|
| 3,318,774 | 5/1967 | Dingwall et al. | 424/549 |
| 3,458,397 | 7/1969 | Myers et al. | 424/549 |
| 4,294,753 | 10/1981 | Urist | 530/395 |
| 4,394,370 | 7/1983 | Jefferies | 424/549 |
| 4,434,094 | 2/1984 | Seyedin et al. | 424/549 |
| 4,440,750 | 4/1984 | Glowacki et al. | 424/549 |
| 4,455,256 | 6/1984 | Urist | 530/350 |
| 4,563,350 | 1/1986 | Nathan et al. | 424/549 |
| 4,596,574 | 6/1986 | Urist | 623/16 |
| 4,608,199 | 8/1986 | Caplan et al. | 530/414 |
| 4,619,989 | 10/1986 | Urist | 530/417 |
| 4,620,327 | 11/1986 | Caplan et al. | 514/21 |
| 4,627,853 | 12/1986 | Campbell et al. | 623/16 |
| 4,627,982 | 12/1986 | Seyedin et al. | 514/21 |
| 4,637,931 | 1/1987 | Schmitz | 424/549 |
| 4,681,763 | 7/1987 | Nathanson et al. | 424/549 |
| 4,743,259 | 5/1988 | Bolander et al. | 514/21 |
| 4,761,471 | 8/1988 | Urist | 530/350 |
| 4,774,227 | 9/1988 | Piez et al. | 514/21 |
| 4,774,228 | 9/1988 | Seyedin et al. | 514/21 |
| 4,774,322 | 9/1988 | Seyedin et al. | 530/353 |
| 4,789,663 | 12/1988 | Wallace et al. | 514/21 |
| 4,789,732 | 12/1988 | Urist | 530/350 |
| 4,795,467 | 1/1989 | Piez et al. | 623/16 |
| 4,795,804 | 1/1989 | Urist | 530/350 |
| 4,804,744 | 2/1989 | Sen | 530/350 |

(List continued on next page.)

OTHER PUBLICATIONS

PNAS, vol. 84, issued Oct. 1987, Sampeth et al, "Isolation of osteogenin . . . ", pp. 7109–7113.
Bone and Mineral Research, vol. 3, Chap. 2, ed. Peck, published 1985 by Elsevier, Reddi, "Regulation of Bone Differentiation By Local And Systemic . . . ".
Laboratory Med., vol. 13, No. 5, issued May 1982, (List continued on next page.)

Primary Examiner—Jeffrey E. Russel
Attorney, Agent, or Firm—Sheridan Ross & McIntosh

[57] ABSTRACT

A method for purifying bone-derived osteoinductive factors including an ultrafiltration process, an anion exchange process, a cation exchange process, and a reverse phase HPLC process. The ultrafiltration process preferably includes a first ultrafiltration step using a membrane having a nominal molecular weight cutoff of approximately 100 kilodaltons (kD) and a second ultrafiltration step employing a membrane having a nominal molecular weight cutoff of approximately 10 kD. For the anion exchange process, a strongly cationic resin is used, preferably having quaternary amine functional groups. Typically, the eluant for the anion exchange process has a conductivity from about 10,260 micromhos ($\mu$mhos) ($1.026 \times 10^{-2}$ siemens (S)) to about 11,200 $\mu$mhos ($1.120 \times 10^{31}$ $^2$ S). For the cation exchange process, a strongly anionic resin is used, preferably having sulfonic acid functional groups. The eluant for the cation exchange process typically has a conductivity from about 39,100 $\mu$mhos ($3.91 \times 10^{-2}$ S) to about 82,700 $\mu$mhos ($8.27 \times 10^{-2}$ S) or more. The HPLC process typically utilizes a column containing hydrocarbon-modified silica packing material. The osteoinductive proteins can be eluted from the HPLC column with an acetonitrile solution in combination with aqueous trifluoracetic acid. The purification processes yield osteoinductively active protein mixtures.

35 Claims, 2 Drawing Sheets

SDS-POLYACRYLAMIDE GEL OF OSTEOINDUCTIVELY ACTIVE PROTEINS FROM HPLC

U.S. PATENT DOCUMENTS

| | | | |
|---|---|---|---|
| 4,810,691 | 3/1989 | Seyedin et al. | 514/21 |
| 4,843,063 | 6/1989 | Seyedin et al. | 514/21 |
| 4,863,732 | 9/1989 | Nathan et al. | 514/21 |
| 4,877,864 | 10/1989 | Wang et al. | 514/12 |
| 4,888,366 | 12/1989 | Chu et al. | 523/115 |
| 4,968,590 | 11/1990 | Kuberasampath et al. | 530/326 |
| 4,975,526 | 12/1990 | Kuberasampath et al. | 530/350 |
| 4,975,527 | 12/1990 | Koezuka et al. | 530/356 |
| 4,992,226 | 2/1991 | Piez et al. | 623/66 |
| 5,001,169 | 3/1991 | Nathan et al. | 514/21 |
| 5,168,050 | 12/1992 | Hammonds, Jr. et al. | 530/350 |
| 5,169,837 | 12/1992 | Lagarde et al. | 530/840 |

OTHER PUBLICATIONS

Block et al, "Glycol Methacrylate Embedding...", pp. 290–298.

Harris et al, Protein Purification Methods—a practical approach, published 1989 by IRL Press (N.Y.), pp. 62, 126, 127, 142, 202, 203, 211, 230–232.

GRADE = 0  1  2  3  4

OSTEOINDUCTIVE PROTEIN MIXTURES AND PURIFICATION PROCESSES

This is a division of application Ser. No. 07/689,459, filed Apr. 22, 1991, now U.S. Pat. No. 5,290,673.

FIELD OF THE INVENTION

The present invention relates generally to proteins useful in inducing or promoting bone growth (i.e. osteoinductive proteins) and to processes used to purify such proteins from extracts of demineralized bone. More specifically, the invention relates to an ultrafiltration process, an anion exchange process, a cation exchange process, and a reverse phase high performance liquid chromatography (HPLC) process, preferably employed in combination, to purify bone-derived proteins.

BACKGROUND OF THE INVENTION

Bones include many proteins, some of which induce or promote bone growth. A great deal of research has been directed to producing, either by recombinant DNA techniques or by purification of naturally occurring proteins, specific osteoinductive proteins. Such proteins and a variety of processes for obtaining them are the subject of numerous patents. However, very little work has been directed to the economic, large scale commercial production of useful osteoinductive proteins.

Collagen Corporation of Palo Alto, Calif. is the assignee of a number of patents directed to osteoinductive proteins. U.S. Pat. No. 4,434,094 by Seyedin et al., issued Feb. 28, 1984 identifies a process to partially purify an osteogenic factor and isolate a non-fibrous protein having a molecular weight less than 30 kilodaltons (kD) from demineralized bone extract using cation exchange chromatography. A partially purified bone-inducing factor of 10 to 30 kD and the purification process including extraction from demineralized bone, gel filtration, and cation exchange chromatography on a carboxymethyl cellulose column, and which may include reverse phase-high performance liquid chromatography (HPLC), is described in U.S. Pat. No. 4,627,982 by Seyedin et al., issued Dec. 9, 1986. Also by Seyedin et al. and assigned to Collagen Corp., U.S. Pat. No. 4,774,228 issued Sep. 27, 1988, describes two 26 kD proteins found in bone having activity in a TGF-$\beta$ assay and purified using a process similar to that taught in Seyedin's '094 patent but including reverse phase HPLC or acetic acid-urea gel electrophoresis, where the purified proteins exhibit chondrogenic activity (purportedly related to bone formation). U.S. Pat. No. 4,863,732 by Nathan et al., issued Sep. 5, 1989 is directed to an injectable solution of an osteogenic factor such as that described in Seyedin's '982 patent, combined with atelopeptide collagen and further purified by coprecipitation. Other patents relate to mixtures of atelopeptide collagen material, e.g. U.S. Pat. Nos. 4,789,663 by Wallace et al., issued Dec. 6, 1988 and 4,795,467 by Piez et al. issued Jan. 3, 1989.

Marshall R. Urist is an inventor named in numerous patents in the field of bone inducing agents. U.S. Pat. No. 4,294,753 by Urist, issued Oct. 13, 1981, describes a process for obtaining bone morphogenetic protein (BMP) by treating demineralized bone with a neutral salt to transform the bone collagen to gelatin, extracting the BMP with a solubilizing agent, then removing the solubilizing agent and salt by dialysis to precipitate the BMP. It is recognized that precipitation of proteins from solution is not highly selective. The BMP, with a molecular weight ranging from 1,000 to 100,000 is the subject of U.S. Pat. No. 4,455,256 by Urist, issued Jun. 19, 1984. U.S. Pat. No.4,619,989 by Urist, issued Oct. 28, 1986, discloses an improved process for further purifying and isolating human and bovine BMP compositions and factors, including additional dialysis and co-precipitation steps. U.S. Pat. No. 4,761,471 by Urist issued Aug. 2, 1988 relates to products obtained by the aforementioned process including a substantially pure BMP composition containing an active 17.5 kD (human) or 18.5 kD (bovine) BMP factor and BMP associated proteins with molecular weights of approximately 14, 22, 24, and 34 kD which may enhance but do not induce bone formation.

U.S. Pat. No. 4,877,864 by Wang, et al., issued Oct. 31, 1989 discloses human and bovine bone inductive factors of approximately 28 kD to 30 kD and characterized by a specific peptide sequence, which may be produced by recombinant gene techniques.

U.S. Pat. No. 4,804,744 by Sen, issued Feb. 14, 1989 identifies a primary osteogenic protein ($P_3$) with a molecular weight of about 22 to 24 kD. This patent also identifies proteins $P_2$ and $P_4$ which are nonosteogenic without $P_3$, and further identifies a method for isolating $P_3$ from demineralized bone tissue including extractions, dialysis, gel filtration and HPLC steps.

As is apparent, it would be desirable to have a mixture of proteins which are highly osteoinductively active. It would be beneficial if such proteins could be produced efficiently and effectively on a commercial scale. It would also be beneficial if such proteins could be produced in a manner designed to minimize degradation of such proteins while maximizing production. It would also be beneficial if such proteins could be produced using relatively well-known unit operations in a process which is tolerant of minor variations in process conditions. It would also be beneficial if the mixture of proteins could be produced directly, without having to first obtain single specific proteins and remix them to attain the desired mixture.

SUMMARY OF THE INVENTION

The present invention includes a process for obtaining an osteoinductive factor, preferably by purification from bovine bone, and the resulting product.

One embodiment of the process for purifying osteoinductively active proteins comprises conducting anion exchange chromatography on a demineralized bone extract solution, preferably having a pH from about pH 8 to about pH 9 and preferably having a conductivity below about 1,900 $\mu$mhos ($1.9 \times 10^{-3}$ S). Proteins are eluted from the anion exchange resin with an eluant, preferably having a conductivity from about 10,260 $\mu$mhos ($1.026 \times 10^{-2}$ S) to about 11,200 $\mu$mhos ($1.120 \times 10^{-2}$ S). The solution of eluted proteins is preferably adjusted to a pH from about pH 4.4 to about pH 5.0 and preferably to a conductivity from about 17,900 $\mu$mhos ($1.79 \times 10^{-2}$ S) to 19,200 $\mu$mhos ($1.92 \times 10^{-2}$ S) and is loaded onto cation exchange resin. Proteins are eluted from the cation exchange resin with an eluant, preferably having a conductivity from about 39,100 $\mu$mhos ($3.91 \times 10^{-2}$ S) to about 82,700 $\mu$mhos ($8.27 \times 10^{-2}$ S). Conductivity values higher than 82,700 $\mu$mhos can also be successfully employed, however, higher values would require a longer time period to dialyze prior to HPLC. The proteins eluted from the cation exchange resin are loaded onto a reverse phase HPLC column. Proteins are eluted from the HPLC column with an eluant having an increasing acetonitrile concentration gradient, preferably ranging from about 33 percent by volume to 37 percent by volume, to obtain a purified mixture of proteins having enhanced osteoinductive activity.

In a further embodiment of the invention, the anion exchange resin is strongly positive and has quaternary amine functional groups. In another embodiment of the invention, the cation exchange resin is strongly negative and has sulfonic acid functional groups. The invention also includes the use of a HPLC packing material which is a hydrocarbon-modified silica and preferably, is a VYDAC TM (The Separation Group) $C_{18}$ column.

The invention also includes an osteoinductive factor obtained by the above-described process. In one embodiment of the osteoinductive factor, the factor is a mixture of a number of proteins having the sodium dodecyl sulfate polyacrylamide gel electrophoresis (SDS-PAGE) profile shown in FIG. 1. Another embodiment of the present invention is a mixture of proteins having a preferred amino acid composition of about 23.4 mole percent of acidic amino acids [ASP(+ASN) and GLU(+GLN)]; about 13.5 mole percent of hydroxy amino acids (SER and THR) about 40.0 mole percent aliphatic amino acids (ALA, GLY, PRO, MET, VAL, ILE, and LEU); about 6.8 mole percent aromatic amino acids (TYR and PHE); and about 16.6 mole percent basic amino acids (HIS, ARG and LYS). TRP, CYS and ½ CYS were not measured and are not included in the calculation of mole percent.

In accordance with a preferred embodiment of the present invention, demineralized bone particles are subjected to protein extraction using guanidine hydrochloride. The extract solution is filtered, and subjected to a two step ultrafiltration process. In the first ultrafiltration step an ultrafiltration membrane having a nominal molecular weight cut off (MWCO) of 100 kD is preferably employed. The retentate is discarded and the filtrate is subjected to a second ultrafiltration step using an ultrafiltration membrane preferably having a nominal MWCO of about 10 kD. The retentate is then subjected to diafiltration to substitute urea for guanidine. The protein-containing urea solution is then subjected to sequential ion exchange chromatography, first anion exchange chromatography followed by cation exchange chromatography. In the process described above, the osteoinductively active proteins are advantageously kept in solution. Preferably, the osteoinductive proteins produced by the above process are then subjected to HPLC.

An advantage of the present invention is that a process is provided which can be readily scaled up to a commercial production scale. A further advantage is that the proteins are kept in solution during the purification steps. Another advantage is that the proteins exhibit little deterioration during the production process. Another advantage is that, if desired, the resultant mixture of proteins can be used directly, without remixing with proteins produced by separate processes.

DETAILED DESCRIPTION OF THE INVENTION

In accordance with the present invention, a process for purifying an osteoinductive factor from bone is provided and an osteoinductive factor is provided.

In one embodiment of the invention, the process for purifying bone derived proteins includes an ultrafiltration step, an anion exchange chromatography step, and a cation exchange chromatography step. Other embodiments of the invention include an HPLC purification step.

Figure 1:
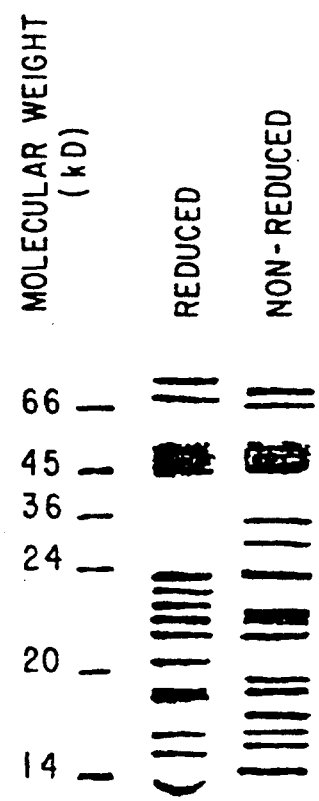
FIG. 1 illustrates an SDS-PAGE of the osteoinductively active protein mixture, both in reduced and nonreduced forms, obtained in accordance with the process of the present invention.

Another aspect of the invention is an osteoinductive mixture of proteins. In one embodiment, the mixture includes several proteins. This is illustrated in FIG. 1 which shows an SDS-PAGE of the reduced and non-reduced osteoinductive factor. In another embodiment the invention also includes an osteoinductively active mixture of proteins with an amino acid composition of about 20.7 to about 26.1 (preferably about 23.4) mole percent of ASP (+ASN) and GLU(+GLN); about 11.3 to about 15.7 (preferably about 13.5) mole percent SER and THR; about 37.6 to about 42.4 (preferably about 40.0) mole percent ALA, GLY, PRO, VAL, MET, ILE, and LEU; about 5.8 to about 7.9 (preferably about 6.8) mole percent TYR and PHE; and about 13.3 to about 19.9 (preferably about 16.6) mole percent HIS, ARG, and LYS. Further embodiments include the osteoinductive factors resulting from each embodiment of the described purification process.

An "osteoinductive factor" as used herein refers to a composition containing one or more proteins which is osteoinductively active as determined by a histological evaluation showing the de novo formation of bone with accompanying osteoblasts, osteoclasts, and osteoid matrix. For example, osteoinductive activity can be demonstrated by a test using a substrate onto which material to be tested is deposited. A substrate with deposited material is implanted subcutaneously in a test animal. The implant is subsequently removed and examined microscopically for the presence of bone formation including the presence of osteoblasts, osteoclasts, and osteoid matrix.

A preferred starting material for the present process is obtained by a multi-step procedure which preferably includes preparing the bone for extraction of proteins by grinding, cleaning, and demineralizing the bone; extracting the bone proteins; and concentrating the extracted proteins with multiple purification steps. The preferred source of starting material for the present process is mammalian bone. Because of its ready availability and low costs, bovine bone is typically used. Other mammalian bone, however, can be suitable for practicing the invention. The bone is prepared for extraction of bone proteins by customary means known in the art, such as grinding and cleaning the bone. Typically, the bone is ground into successively finer particles and soaked in detergent solution to remove non-bone material. Preferably the bone is ground to particles less than 4 mm in size and preferably from about 1 mm to about 4 mm in size, soaked in detergent solution between grindings, and rinsed in a flotation tank to remove soft tissue.

The cleaned ground bone is then demineralized with acid. The bone is soaked in any suitable acid and may be agitated, preferably at room temperature. The pH of the acid soaking solution typically is maintained at or below pH 1.3. A solution of dilute HCl (e.g. from about 0.6M to about 1.2M) has proven effective to demineralize bone. Alternatively other suitable acids such as formic acid can be used. Octyl alcohol or other defoaming agents are useful to prevent exessive foaming during demineralization.

The bone is soaked in acid for sufficient time until the bone is substantially completely demineralized. X-ray analysis may be used to evaluate the extent of demineralization. Alternatively, standard procedures can be developed through experience to determine the amount of time required for demineralization. Typically, at least seven hours is required. The demineralized bone is then rinsed to remove the acid. Typically the bone is rinsed with water overnight or until the pH of the rinse discharge reaches pH 4 or more. As will be appreciated by those skilled in the art, alternative cleaning and demineralizing processes can also be employed.

Proteins are extracted from the demineralized bone using a protein denaturant such as guanidinium ion and/or urea. Preferably the extraction is performed at less than 20° C. and more preferably at less than 15° C. It should be noted that other suitable denaturants can be used as well. Guanidine hydrochloride is a preferred denaturant because it is ionic and therefore also functions well as a solubilizing agent for maintaining proteins in solution.

Optionally, a chaotrope can be added during extraction to improve solubility of extracted proteins. Suitable chaotropes include calcium chloride ($CaCl_2$), magnesium chloride ($MgCl_2$), and cesium chloride ($CeCl_2$).

Protein can be extracted from demineralized bone by means typically used in the art. For example, a protein denaturant can be pumped through demineralized bone in a filter press to extract proteins in recovered denaturant. In order to provide appropriate low temperatures, the denaturant can be cooled to an initially low temperature, preferably from about 0° C. to about 4° C., as it is pumped through the demineralized bone. The temperature of the denaturant can increase during the extraction process.

Usually, extraction continues until substantially all of the noncollagenous bone proteins have been removed from the demineralized bone. A typical extraction takes about 48 hours. Preferably the extraction solution is maintained near neutral pH.

The extracted proteins in a denaturant solution are separated by a series of purification steps. A first ultrafiltration process selects for desired proteins with a molecular weight within a preselected, desired range for further processing. Preferably, as a first step, an ultrafiltration membrane with a 100 kD nominal molecular weight cutoff (MWCO) is used, such as a plate and frame tangential flow filtration unit sold under the trade name "Centrasette" TM (Filtron). The filtration is preferably conducted under pressure and typically at about 50 psi filtration pressure. The protein concentration will vary depending on the completeness of the extraction.

Following the first ultrafiltration step, the filtrate is concentrated by a second ultrafiltration step, preferably across a 10 kD nominal molecular weight cutoff membrane, which eliminates lower molecular weight proteins. The second ultrafiltration yields a retentate with a mixture of proteins having molecular weights within a desired range ("filtered protein concentrate").

In a preferred embodiment, in preparation for subsequent ion exchange chromatography, the filtered protein concentrate is transferred from an ionic denaturant solution to a non-ionic denaturant solution, such as urea. A non-ionic denaturant is preferred for use in the subsequent ion exchange purification steps because an ionic denaturant, such as guanidine hydrochloride, impairs the ability of the ion exchange resins to selectively bind desired proteins. Preferably, the protein denaturant solution is from about 2M to about 6M urea solution which is buffered with tris[hydroxymethyl]aminomethane (hereinafter referred to as "tris") and titrated to pH of about pH 8.5.

The transfer of proteins from an ionic to a non-ionic denaturant can be accomplished using diafiltration or dialysis. Diafiltration is performed using a suitable tangential flow ultra-filtration unit such as a Centrasette TM (Filtron) ultrafiltration unit. Through the use of diafiltration or dialysis the filtered protein concentrate can be transferred to the appropriate denaturant without precipitation of proteins from solution. This procedure is advantageous because it simplifies subsequent purification and prevents losses that can occur if proteins are allowed to precipitate. It is also advantageous that this procedure can be used on a commercial production scale.

The present invention includes an anion exchange process to purify a solution of extracted bone proteins to yield an osteoinductively active mixture of proteins. In a preferred embodiment of the anion exchange process, the starting material is prepared using the above-described process for obtaining a preferred starting material. The anion exchange process is combined with additional purification processes described below.

In ion exchange chromatography, i.e., anion exchange and cation exchange chromatography, the affinity of a particular protein for a particular ion exchange resin depends on the ionic strength of the protein solution and pH. The ionic strength of a solution can be measured by its conductivity. Alternatively, the ionic strength of a solution can be measured in terms of a specific counterion concentration. As used herein, the term "counterion concentration" refers to the molar concentration of an ion in solution which competes with proteins for binding sites on the ion exchange resin.

Prior to loading a bone protein solution onto an anion exchange column in accordance with the present invention, the conductivity of the bone protein solution is adjusted to allow the desired proteins to bind selectively to the resin. In the present anion exchange process, the conductivity of the bone protein solution is adjusted to less than about 1,900 $\mu$mhos ($1.9 \times 10^{-3}$ S), and more preferably from about 1,080 $\mu$mhos ($1.08 \times 10^{-3}$ S) to about 1,900 $\mu$mhos ($1.9 \times 10^{-3}$ S) by variation in the counterion concentration. In a preferred embodiment, the counterion is $Cl^-$ and is present in a concentration of less than about 0.135M NaCl.

The bone protein solution to be purified by the anion exchange process, having an appropriate conductivity, is loaded onto an anion exchange column. In the present anion exchange process, the anion exchange column has a strongly positive anion exchange resin. It has been found that the present anion exchange process with a strongly positive anion exchange resin is effective in purifying an osteoinductively active mixture of proteins. As used herein, the term strongly positive anion exchange resin refers to a resin having strongly positive functional groups such as quaternary amine functional groups. A preferred resin with quaternary amine functional groups is sold under the trademark "Q-Sepharose"™ (Pharmacia). However, other resins having similarly basic functional groups are suitable as well.

A further factor affecting the selectivity of binding to the anion exchange resin is the pH of the bone protein solution being loaded onto the anion exchange column and the anion exchange eluant. The pH of the bone protein solution and eluant is at a pH effective to allow the resin to bind desired proteins from the bone protein solution as it passes through the column and to allow for desired elution of proteins. Generally, a pH of between about pH 8 and pH 9 is effective in the present process. Preferably, the pH of the protein solution and eluant is adjusted to about pH 8.5.

The linear velocity of the bone protein solution through the anion exchange column is determined by required recovery parameters. Typically, the process is run at a low velocity to allow for substantially complete adsorption of desired proteins so that protein loss is minimized. It should be recognized, however, that the linear velocity can be greater, but that protein loss may be sustained.

The anion exchange process further includes selectively desorbing a desired fraction of bound proteins from the column resin with an eluant. The fraction of bound proteins which are desorbed is determined by the conductivity of the eluant solution. Proteins are eluted from the anion exchange column of the present invention with a solution having a conductivity sufficient to obtain an osteoinductively active protein mixture. Preferably, the eluant has a conductivity from about 10,260 $\mu$mhos ($1.026 \times 10^{-2}$ S) to about 11,200 $\mu$mhos ($1,120 \times 10^{-2}$ S). Higher conductivities may be employed, however, this leads to the desorption of a greater amount of materials which may have to be removed during a subsequent purification step.

The anion exchange eluant in the present invention is typically a protein denaturant solution having an appropriate salt concentration to obtain the appropriate conductivity. A preferred eluant is 6M urea buffered with tris base containing sodium chloride. Sodium chloride (NaCl) is effective to provide a counterion concentration which yields the appropriate conductivity in the eluant. In a preferred embodiment, the eluant is prepared with a counterion concentration of NaCl between about 0.10M and about 0.16M and more preferably between about 0.105M and about 0.145M. Other suitable salts may also be used at a counterion concentration sufficient to provide the appropriate conductivity.

The present invention further includes a cation exchange chromatography process to further purify the osteoinductive factor from bone-derived proteins in solution which may be used advantageously in combination with the anion exchange process described above and the HPLC process described below.

As discussed above with respect to the anion exchange process, the conductivity of the bone protein solution is controlled to effect selective binding of proteins to the cation exchange resin. Prior to loading the bone protein solution onto a cation exchange column in the present invention, the conductivity of the bone protein solution is adjusted to be effective to allow the cation exchange resin to selectively bind a desired fraction of proteins. In the present cation exchange process, the conductivity of the bone protein solution is preferably from about 17,900 $\mu$mhos ($1.79 \times 10^{-2}$ S) to about 19,200 $\mu$mhos ($1.92 \times 10^{-2}$ S). Sodium chloride or other suitable salt can be used to adjust the conductivity to an appropriate level. In a preferred embodiment, the counterion concentration of the bone protein solution is between about 0.125M NaCl and about 0.30M NaCl, and more preferably between about 0.23M and about 0.27M NaCl.

The bone protein solution to be purified by the cation exchange process, having an appropriate conductivity, is loaded onto a cation exchange column. In the present cation exchange process, a strongly negative cation exchange resin has been found effective in purifying a mixture of osteoinductively active proteins. As used herein, the term strongly negative cation exchange resin refers to a resin having strongly negative functional groups such as sulfonic acid functional groups. A preferred resin with sulfonic acid functional groups is sold under the trademark "S-Sepharose"™ (Pharmacia). However, other resins having similarly acidic functional groups are suitable as well.

The pH of the bone protein solution to be purified by the cation exchange process is adjusted to a pH effective for the binding of desired proteins to the resin. In the present process, a pH of between about pH 4.4 and about pH 5.0 is preferably used. Preferably the pH of the protein solution is adjusted to about pH 4.8.

The linear velocity of the bone protein solution through the cation exchange column, as with the anion exchange above, is determined by required recovery parameters. The velocity is generally sufficiently low to permit substantially complete adsorption of the desired proteins with minimal protein loss.

The cation exchange process further includes selectively desorbing a desired fraction of bound proteins from the column resin. Proteins are eluted from the cation exchange column with an eluant having a conductivity suitable to yield an osteoinductively active protein mixture. For the present cation exchange process, the conductivity of the eluant is preferably from 39,100 $\mu$mhos ($3.91 \times 10^{-2}$ S) to about 82,700 $\mu$mhos ($8.27 \times 10^{-2}$ S) or more.

Generally, the eluant for the present process is a solution having a suitable protein denaturant, such as urea, and an appropriate salt concentration to achieve the desired conductivity. In a preferred embodiment, the eluant is prepared with a counterion concentration from about 0.6M NaCl to about 1.5M NaCl and more preferably from about 1.3M to about 1.5M NaCl to provide the appropriate conductivity.

The present invention further includes a reverse phase HPLC process which may be combined with the anion and cation exchange processes described above to obtain an osteoinductively active mixture of proteins. In the HPLC purification process of the present invention, a bone protein solution is loaded onto a reverse phase HPLC column. This column may be polymeric (i.e., polystyrene) or silica based. Preferably, the HPLC column is a hydrocarbon modified silica. Preferably, a silica resin is modified by the addition of $C_4$–$C_{18}$ hydrocarbon chains, and more preferably, the HPLC column is a VYDAC™ (The Separation Group) $C_{18}$ column.

The bone protein solution to be loaded onto the reversed phase column can be a solution of trifluoroacetic acid or other suitable solvent (e.g. heptafluorobutyric acid or phosphoric acid). Preferably, a trifluoroacetic acid solution is used having a concentration of from about 0.05 percent by volume to about 0.15 percent by volume, and more preferably about 0.1 percent by volume trifluoroacetic acid.

Osteoinductively active proteins are eluted from the HPLC column with an organic solvent/water mixture suitable for obtaining the desired proteins. A preferred eluant in the HPLC process is an acetonitrile solution. The preferred eluant typically has an acetonitrile concentration which varies, during elution, from about 30 percent by volume to about 40 percent by volume and more preferably from about 33 percent by volume to about 37 percent by volume. In preferred embodiments, the acetonitrile concentration in the eluant is increased in increments of between about 0.30 percent by volume and about 0.40 percent by volume per minute until the desired highest concentration of acetonitrile is achieved. Proteins can be recovered from the HPLC process eluant by means generally known in the art.

A further embodiment of the present invention is the protein product from the above-described HPLC process which exhibits osteoinductive activity at about 3 micrograms when deposited onto a suitable carrier and implanted subcutaneously. In one embodiment of the invention, the osteoinductive factor is an osteoinductively active mixture of proteins which exhibit the gel separation profile shown in FIG. 1. This gel separation profile was performed using SDS-PAGE. The first column is a molecular weight scale which was obtained by performing SDS-PAGE on standards of known molecular weight. The second column illustrates the SDS-PAGE profile for a mixture of proteins in accordance with the present invention which have been reduced with 2-mercaptoethanol. The third column illustrates the SDS-PAGE profile for a non-reduced mixture of proteins in accordance with the present invention. Although the mixture of proteins which provide the SDS-PAGE profile illustrated in FIG. 1 have been found to have high osteoinductive activity, as will be demonstrated in the examples, it is anticipated that mixtures of proteins having SDS-PAGE profiles which differ slightly from that illustrated in FIG. 1 will also be effective. Therefore, mixtures of proteins having profiles which comprise substantially all of the protein bands detected in the reduced or nonreduced SDS-PAGE profiles in FIG. 1 will be considered to be within the scope of the invention.

Yet another embodiment of the invention includes an osteoinductively active mixture of proteins having, upon hydrolysis, an amino acid composition of about 23.4 mole percent of ASP(+ASN) and GLU(+GLN); about 13.5 mole percent SER and THR; about 40.0 mole percent ALA, GLY, PRO, MET, VAL, ILE, and LEU; about 6.8 mole percent TYR and PHE; and about 16.6 mole percent HIS, ARG and LYS.

An osteoinductively active mixture of proteins, as derived by any of the above-described processes, or by some other process, can be delivered to a site where bone growth is desired using a variety of delivery systems. One delivery system is a collagen substrate on which an osteoinductively active mixture of proteins is deposited. A further embodiment of the invention is a delivery system using skin-derived or tendon-derived collagen.

EXAMPLES

Example 1

Bovine cortical bone segments (47 kg) were ground through successive screens of 25, 6 and 4 mm pore size. After each grinding, the bone particles were cleaned in a flotation tank containing a detergent solution to facilitate soft tissue and lipid removal. The ground bone (25.95 kg) was demineralized by stirring with 60 gallons of a 1.2M HCl solution for 7.5 hours at room temperature. Forty milliliters of octanol was also added to prevent foaming.

Osteoinductively active proteins were extracted with approximately 60 l of 4M guanidine hydrochloride, buffered with tris base to pH 7.4, by continuously circulating the solution through a packed bed of the demineralized bone particles. The guanidine was initially cooled to about 4° C. during the extraction, in which 59 liters of extract solution was collected after 49.5 hours.

The extract solution was filtered through a 5 μm capsule filter then concentrated to a volume of 700 ml using 25 sq. ft. of Filtron Omega TM tangential flow ultrafiltration membrane with a nominal molecular weight cut-off (MWCO) of 100 kD. The retentate was discarded, and the less than 100 kD MW filtrate was concentrated to a volume of 1.1 l on 25 sq. ft. of Filtron Omega TM ultrafiltration membrane with a nominal MWCO of 10 kD. Thirty l of 20 mM tris and 6M urea, adjusted to pH 8.5 with HCl, was then used to diafilter the solution using the same 10 kD MWCO membrane. The 950 ml of retentate contained approximately 19.27 grams of protein. The filtrate was discarded.

The retentate was loaded onto a Q-Sepharose TM (Pharmacia) anion exchange column (25.2 cm diameter×16.5 cm, bed volume=8.3 l) equilibrated with 20 mM tris and 6M urea, adjusted to pH 8.5 with HCl (conductivity=910 μmhos; $9.1\times10^{-4}$ S). Following sample application, the column was washed with approximately 2 void volumes of equilibration buffer. Osteoinductively active proteins were eluted from the column by applying approximately 12 l of 0.125M NaCl in 20 mM tris and 6M urea, adjusted to pH 8.5 (conductivity=10,740 μmhos; $1.074\times10^{-2}$ S). Approximately 3.94 g of protein in 11 l were recovered in the column eluate.

Eluate from Q-Sepharose TM (Pharmacia) anion exchange chromatography was adjusted to pH 4.8 with glacial acetic acid and the conductivity was increased to 18,200 μmhos ($1.82\times10^{-2}$ S) by adding solid NaCl. The sample was then loaded onto an S-Sepharose TM (Pharmacia) cation exchange column (11.3 cm diameter×16.5 cm, bed volume=1.65 l) equilibrated with 0.25M NaCl in 20 mM sodium acetate and 6M urea, adjusted to pH 4.5. Following sample application, the column was washed with approximately 2 void volumes of equilibration buffer. Osteoinductively active proteins were eluted by applying approximately 1.7 l of 1.5M NaCl in 20 mM sodium acetate and 6M urea, adjusted to pH 4.5 (conductivity=79,500 μmhos; $7.95\times10^{-2}$ S). Approximately 220.8 mg of protein in 1.2 l were recovered in the column eluate.

The cation exchange eluate was dialyzed in the cold (4° C.) against deionized water using a 6 kD molecular weight cut off hollow fiber bundle (obtained from Spectrum Industries), in order to remove low molecular weight species, and freeze-dried. It was redissolved in 10 percent (v/v) acetic acid, freeze-dried, then dissolved again in 10 mM HCl. After sequential filtration through 1.2 and 0.45 μm filters, the protein mixture was allowed to stand at room temperature for 18 to 24 hours then freeze-dried.

By the series of steps outlined here, the osteoinductively active proteins were maintained in solution. Protease inhibitors were not used at any step, and no degradation of the proteins was observed. Following cation exchange chromatography and removal of salts and buffers, 35 μg of the proteins isolated by this procedure reproducibly induced bone formation when combined with a suitable carrier or matrix and implanted subcutaneously in rats.

Example 2

The freeze-dried sample from S-Sepharose TM (Pharmacia) cation exchange chromatography was dissolved in 6 ml of a mixture of aqueous 0.1 volume percent trifluoroacetic acid/30 volume percent acetonitrile and applied to a preparative VYDAC TM (The Separation Group) $C_{18}$ wide pore HPLC column equilibrated with 57% A, 43% B (where A is 0.1 volume percent trifluoroacetic acid in water and B is 70 volume percent acetonitrile, 0.1 volume percent trifluoroacetic acid in water). The osteoinductively active proteins were separated from other components of the sample using a shallow gradient of increasing B. Eluate from the HPLC was characterized by SDS-polyacrylamide gel electrophoresis and in vivo bioassay. Osteoinductively active proteins were found to elute between 47 volume percent B and 52 volume percent B (33 percent to 37 percent acetonitrile by volume). Proteins eluting over this range of solvent composition were freeze-dried, then dissolved in 10mM HCl. The yield of osteoinductively active proteins was 16.45 mg. When deposited on a suitable carrier or matrix and implanted subcutaneously, 3.5 μg of this protein mixture induced bone formation.

Example 3

There are a number of characteristic protein bands which are present in the osteoinductively active pool. They range between 14 kD and 68 kD apparent MW based on electrophoretic migration in 15 weight percent SDS-polyacrylamide gels. Examples of the protein banding pattern before and after reduction with 2-mercaptoethanol are illustrated in FIG. 1.

Example 4

Aliquots from the osteoinductively active pool from preparative HPLC were hydrolyzed in 6M HCl vapor at 110° C. for 20 hours under an argon atmosphere. Hydrolyzed samples were derivatized with phenylisothiocyanate to form the PTC-amino acid derivatives, and analyzed by reversed phase HPLC using a Beckman 338 gradient system equipped with System Gold software. Three amino acid analyses were averaged to establish the composition presented in Table I.

TABLE I

| Amino Acid | Mole Percent |
|---|---|
| Asp | 11.14 |
| Glu | 12.25 |
| Ser | 9.48 |
| Gly | 8.50 |
| His | 2.28 |
| Arg | 7.19 |
| Thr | 4.03 |
| Ala | 8.05 |
| Pro | 7.16 |
| Tyr | 3.63 |
| Val | 3.79 |
| Met | 1.73 |
| Ile | 2.75 |
| Leu | 8.00 |
| Phe | 3.21 |
| Lys | 7.11 |

Example 5

Evaluation of the osteoindictive activity of purified and partially purified osteoinductive factor.

A sufficient quantity of purified Type I fibrillar bovine tendon collagen was added to a 1 volume percent solution of acetic acid in water to make a 4 weight percent dispersion. After standing overnight at room temperature, the viscous dispersion was placed into a multicavity DELRIN TM (DuPont) mold making discs 8 mm in diameter × 3 mm thick. The mold of collagen dispersion was frozen at −50° C. and lyophilized for about eighteen hours yielding discs of collagen sponge weighing 6.0±1 mg each. These discs served as the substrate to which the osteoinductive factor was added during the in vivo biological evaluation of osteoinductive activity.

PURIFIED OSTEOINDUCTIVE FACTOR

To a $1 \times 10^{-2}$M solution of hydrochloric acid was added a sufficient quantity of purified osteoinductive factor to prepare test solutions containing 35,100 and 350 μg of protein per ml HCl. One hundred μl aliquots of the above three test solutions were added to four collagen sponge discs for each test dose. The solution was allowed to soak into the collagen sponge discs for thirty minutes whereupon the discs were frozen at −50° C. and lyophilized for about eighteen hours. These purified osteoinductive factor-containing collagen sponge discs were implanted subcutaneously in four rats in a manner similar to that described by Reddi (Reddi, A. H., "Regulation of Bone Differentiation by Local and Systemic Factors" in *Bone & Mineral Research*, Vol. 3, Chap. 2, ed. William Peck (Elsevier Publishers B. V., 1985) which is incorporated herein by reference in its entirety) and as described below.

A small (≈6 mm) incision was made in the skin of the ventral thorax region of a female Long-Evans rat, weighing approximately 50 to 100 g. A pocket was prepared beneath the skin by blunt dissection. One of the previously prepared collagen sponge discs containing purified osteoinductively active protein was inserted in the pocket and the incision was closed with Tevdek II TM (Ethicon) 5-0 sutures. One each of the other two purified osteoinductively active protein dose group samples were similarly implanted in each animal. The implanted collagen sponge discs were separated from each other by a minimum of 1 cm distance. After 21 days, the rats were sacrificed by asphyxiation with carbon dioxide and the test materials were removed. At explantion, the tissue samples were weighed and fixed in 70 percent ethanol. After at least four hours of fixation, the explanted tissues were x-rayed using a Micro-R x-ray cabinet, (20 keV x-rays, Polaroid Type 53 film, 20 second exposure time). The explanted tissue samples were embedded using polymerized glycol methacrylate (see Block, M. H., L. Trenner, P. Reugg, and M. Karr, "Glycol Methacrylate Embedding Technique", *Laboratory Medicine*, 13(5): 1982, pp. 290–298, which is incorporated herein by reference in its entirety), sectioned at a 4 micron thickness, stained with Toluidine Blue O or silver nitrate followed by hematoxylin and eosin, and evaluated histologically for osteogenesis and calcified tissue proliferation. Endochondral bone formation (as judged by explant mass measurements, x-ray evaluation and histologic evaluation) was readily demonstrated. The results are summarized in Table II below.

TABLE II

Figure 2:
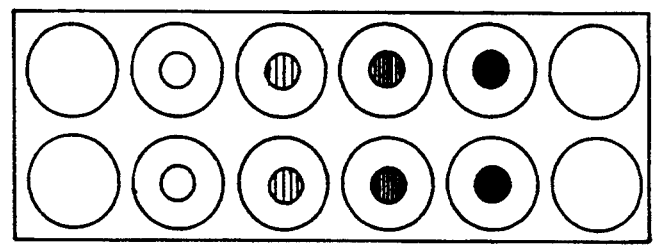
FIG. 2 illustrates the x-ray standards employed to obtain the "X-Ray Score" employed in the Examples.

| Purified OF Dose | Mass of Subcutaneous Explant (X ± SD mg) | X-Ray Score (See FIG. 2) | Histologic Grade (See Table IV) |
|---|---|---|---|
| Zero | NSF* | NSF | NSF |
| 3.5 μg | 75.5 ± 4.9 | 3.0 | 3.0 |
| 10 μg | 104.8 ± 11.2 | 4.0 | 3.5 |
| 35 μg | 109 ± 9.1 | 4.0 | 4.0 |

*NSF = No Sample Found

PARTIALLY PURIFIED OSTEOINDUCTIVE FACTOR

Partially purified osteoinductive factor material was evaluated using these same procedures. A protein sample obtained following cation exchange chromatography but prior to HPLC purification was dissolved in $1 \times 10^{-2}$M hydrochloric acid at concentrations of 350, 100 and 3,500 μg of protein per ml HCl. One hundred μl aliquots of the above three test solutions were added to four collagen sponge discs for each test done. The solutions were allowed to soak into the collagen sponge discs for thirty minutes. The discs were then frozen at −50° C. and lyophilized for about eighteen hours. These discs containing partially purified osteoinductive factor were implanted subcutaneously in rats. After 21 days the tissues were explanted and evaluated by the procedures described above. The results are summarized in Table III below.

TABLE III

| Purified OF Dose | Mass of Subcutaneous Explant (X ± SD mg) | X-Ray Score (See FIG. 2) | Histologic Grade (See Table IV) |
|---|---|---|---|
| Zero | NSF* | NSF | NSF |
| 35 μg | 52.8 ± 15.3 | 2.5 | 1.75 |
| 100 μg | 100 ± 14.1 | 3.5 | 3.25 |
| 350 μg | 116 ± 8.5 | 3.75 | 3.75 |

*NSF = No Sample Found

As can be appreciated by comparing Table II to Table III, the purified osteoinductive factor provides much greater osteoinductive activity at lower dosages than the partially purified osteoinductive factor. For this reason, the purified osteoinductive factor is preferred.

TABLE IV

SCORING CHARACTERISTICS FOR SUBCUTANEOUS IMPLANT BIOASSAY SAMPLES

| SCORE | CHARACTERISTIC HISTOLOGIC APPEARANCE |
|---|---|
| Zero | No residual implanted sample found, OR section shows no silver staining deposits or those deposits are associated with acellular events, e.g., dystrophic mineralization of collagen fibrils. Explants generally small, 2–4 mm diameter. |
| One (1) | Tissue explant diameters generally smaller (3–5 mm) than original implants (7–8 mm). Focal areas of silver staining mineralized tissues are of cellular origin. This may include mineralized cartilage as well as mineralized osteoid matrix. Silver staining deposits randomly distribute within the explanted tissue section. Silver stained areas typically encompass less than 50% of the total section area. Explant centers are infiltrated with fibroblast-like cells, show little or no residual fibrillar collagen, and are not infarcted. |
| Two (2) | Larger than grade 1 explants, but not as large as original implanted discs. Silver staining areas generally localized in the outer regions of the explant. Silver staining tissue is substantially all mineralized cartilage or dystrophic mineral radiating inward from mineralized cartilage showing little bone formation or few active osteoblastic surfaces. Little or no hematopoietic bone marr present. Explant centers often show residual, non-resorbed fibrillar collagen sponge. |
| Three (3) | Silver staining mineralized tissue clearly shows a circular pattern occurring near the outer regions of the explant. Both mineralized cartilage and active osteoblast surfaces present. More mature bone forming closest to the periphery of the explant. Hematopoietic bone marrow elements present. Clear evidence for osteoclastic resorption of mineralized cartilage occurring. Dystrophic mineralization often seen toward center of explant inside of the region of true bone formation. Fewer cells present in center of explant than seen in Score 2 samples. Residual collagen sponge often evident. Areas of chondrocyte proliferation often present but not extensive. Blood capillaries invading mineralized area. |
| Four (4) | Silver staining mineralized tissues clearly form as a thin rim of bone at the periphery of the section. Most of the mineralized cartilage has been resorbed. Bone clearly of osteoblastic origin, with many active osteoblast surfaces present. Often large area of proliferating chondrocytes and extracellular matrix evident. Hematopoietic bone marrow present. The "pseudo-periosteum" is thin ($\approx 10$ cell layers) and composed primarily of cells which appear to be fibroblastic. The center of the section often infarcted and largely acellular. |

While various embodiments of the present invention have been described in detail, it is apparent that modifications and adaptations of those embodiments will occur to those skilled in the art. For example, the osteoinductive factors can be used in various applications such as treating periodontal diseases and in facial reconstruction, as well as in treating other bone and joint problems. However, it is to be expressly understood that such modifications and adaptations are within the

What is claimed is:

1. A process for purifying osteoinductively active proteins from a first solution containing demineralized bone extract, comprising:
   (i) subjecting said first solution to a first tangential flow ultrafiltration step to obtain a second solution using an ultrafiltration membrane having a nominal MWCO of approximately 100 kD;
   (ii) subjecting said second solution to a second tangential flow ultrafiltration step to obtain a third solution using an ultrafiltration membrane having a nominal MWCO of approximately 10 kD;
   (iii) loading said third solution onto an anion exchange resin;
   (iv) eluting proteins from said anion exchange resin with a first eluant to obtain an anion exchanged fraction eluate;
   (v) loading said anion exchange fraction eluate onto a cation exchange resin; and
   (vi) eluting proteins from said cation exchange resin with a second eluant to obtain a cation exchanged fraction eluate.

2. A process, as claimed in claim 1 further comprising the step of loading said cation exchanged fraction eluate onto a reverse phase HPLC column.

3. A process, as claimed in claim 1, wherein the conductivity of said third solution from said second tangential flow ultrafiltration step is adjusted, if necessary, to a conductivity of less than about 1,900 $\mu$mhos ($1.9 \times 10^{-3}$ S) prior to loading onto said anion exchange resin.

4. A process, as claimed in claim [8], wherein said first eluant has a conductivity in a range from about 10,260 $\mu$mhos ($1.026 \times 10^{-2}$ S) to about 11,200 $\mu$mhos ($1.120 \times 10^{-2}$ S).

5. A process, as claimed in claim 1, wherein said anion exchanged fraction eluate is adjusted, if necessary, to a conductivity in a range from about 17,900 $\mu$mhos ($1.79 \times 10^{-2}$ S) to about 19,200 $\mu$mhos ($1.92 \times 10^{-2}$ S) prior to loading onto said cation exchange resin.

6. A process, as claimed in claim 1, wherein said second eluant has a conductivity from about 39,100 $\mu$mhos ($3.91 \times 10^{-2}$ S) to about 82,700 $\mu$mhos ($8.27 \times 10^{-2}$ S).

7. A process for purifying osteoinductively active proteins from a first solution containing demineralized bone extract, comprising:
   (i) subjecting said first solution to ultrafiltration to obtain a second solution containing proteins having a molecular weight of less than about 100 kD;
   (ii) loading said second solution onto an anion exchange resin;
   (iii) eluting proteins from said anion exchange resin with a first eluant to obtain an anion exchanged fraction eluate;
   (iv) loading said anion exchanged fraction eluate onto a cation exchange resin;
   (v) eluting proteins from said cation exchange resin with a second eluant to obtain a cation exchanged fraction eluate;
   (vi) loading said proteins from said cation exchanged fraction eluate onto a reverse phase HPLC column; and
   (vii) eluting proteins from said HPLC column with a third eluant having a gradient of increasing acetonitrile concentration ranging from about 30 percent by volume to about 40 percent by volume to obtain a purified mixture comprising osteoinductively active proteins.

8. A process, as claimed in claim 7, wherein said gradient of increasing acetonitrile concentration of said third eluant increases from about 33 percent by volume to about 37 percent by volume.

9. A process, as claimed in claim 1, wherein said anion exchange resin comprises quaternary amine functional groups.

10. A process, as claimed in claim 1, wherein said cation exchange resin comprises sulfonic acid functional groups.

11. A process, as claimed in claim 7, wherein said HPLC column comprises either a plastic or hydrocarbon-modified silica packing.

12. A process, as claimed in claim 11, wherein said silica is modified by the addition of $C_4$ through $C_{18}$ hydrocarbons.

13. A process, as claimed in claim 7, wherein said HPLC column comprises a packing material selected from the group consisting of silica resin modified by the addition of $C_4$, $C_8$ or $C_{18}$ material.

14. A process, as claimed in claim 1, wherein the pH of said third solution is from about pH 8 to about pH 9 prior to said step of loading said third solution onto said anion exchange resin.

15. A process, as claimed in claim 1, wherein the pH of said anion exchanged fraction eluate is from about pH 4.4 to about pH 5.0 prior to said step of loading said anion exchanged fraction eluate onto said cation exchange resin.

16. A process, as claimed in claim 1, wherein said third solution, said anion exchanged fraction eluate and said cation exchanged fraction eluate comprise an effective amount of urea to maintain proteins therein in solution.

17. A process, as claimed in claim 1, wherein said third solution has a counterion concentration less than about 0.135M NaCl prior to loading onto said anion exchange resin.

18. A process, as claimed in claim 1, wherein said first eluant has a counterion concentration in a range from about 0.23M NaCl to about 0.27M NaCl.

19. A process, as claimed in claim 1, wherein said second eluant has a counterion concentration in a range from about 0.6M NaCl to about 1.5M NaCl.

20. A process, as claimed in claim 7, wherein said third solution comprises from about 0.05 percent by volume to about 0.15 percent by volume trifluoracetic acid.

21. A process, as claimed in claim 7, wherein said acetonitrile concentration in said third eluant is increased from about 33 percent by volume in increments of between about 0.30 percent by volume and about 0.40 percent by volume per minute until said concentration is about 37 percent by volume acetonitrile.

22. A process, as claimed in claim 1, wherein said first solution containing demineralized bone extract is prepared by extracting proteins from cleaned, crushed demineralized bone particles using guanidine at a temperature of less than 20° C.

23. A process, as claimed in claim 22, wherein urea is substituted for guanidine in a diafilter or dialysis process.

24. A process, as claimed in claim 1, wherein an osteoinductive factor is produced having, upon hydrolysis, an amino acid composition of from about 20.7 to about 26.1 mole percent ASP(+ASN) and GLU(+GLN); from about 11.3 to about 15.7 mole percent SER and THR; from about 37.6 to about 42.4 mole percent ALA, GLY, PRO, MET, VAL, ILE, and LEU; from about 5.8 to about 7.9 mole percent TYR and PHE; and from about 13.3 to about 19.9 mole percent HIS, ARG, and LYS, wherein said mole percentages are based on the total moles of said ASP(+ASN), GLU(+GLN), SER, THR, ALA, GLY, PRO, MET, VAL, ILE, LEU TYR, PHE, HIS, ARG, and LYS amino acids.

25. A process, as claimed in claim 1 wherein a mixture of proteins is produced which, when subjected to sodium dodecyl sulfate polyacrylamide gel electrophoresis, results in a reduced or nonreduced gel profile comprising substantially all of the protein bands as shown in FIG. 1.

26. A process, as claimed in claim 1, wherein an osteoinductive factor is produced having a mixture of proteins that is soluble in water at a concentration of 10 milligrams of said protein mixture per milliliter of water at room temperature that achieves a histological grade of at least about 3 when subcutaneously implanted for 21 days at a protein:substrate weight ratio of about 1:600.

27. A process, as claimed in claim 1, wherein an osteoinductive factor is produced having a mixture of proteins that comprises an amino acid composition of from about 20.7 to about 26.1 mole percent acidic amino acids, about 11.3 to about 15.7 mole percent hydroxy amino acids, about 37.6 to about 42.4 mole percent aliphatic amino acids, about 5.8 to about 7.9 mole percent aromatic amino acids and about 13.3 to about 19.9 mole percent basic amino acids, wherein said mixture of proteins achieves a histological grade of at least about 3 when subcutaneously implanted for 21 days at a protein:substrate weight ratio of about 1:600.

28. A process, as claimed in claim 1, wherein an osteoinductive factor is produced having the amino acid mole percentages shown in Table I.

29. A process, as claimed in claim 1, wherein an osteoinductive factor is produced having a mixture of proteins which exhibit osteoinductive activity at about 3 micrograms when deposited onto a carrier suitable for induction of bone formation and implanted subcutaneously.

30. A process for purifying osteoinductively active proteins comprising:
(a) crushing bone and cleaning said bone, including the step of removing soft tissue therefrom by flotation, to form crushed and cleaned bone particles;
(b) demineralizing said crushed and cleaned bone particles using an acid;
(c) extracting proteins from the cleaned, crushed and demineralized bone particles using guanidine at low temperature to prevent the deterioration of said proteins and to obtain a first solution;
(d) subjecting said first solution to an ultrafiltration process comprising a first tangential flow ultrafiltration step employing an ultrafiltration membrane having a nominal MWCO of approximately 100 kD, retaining the filtrate and subjecting said filtrate to a second tangential flow ultrafiltration step employing an ultrafiltration membrane having a nominal MWCO of approximately 10 kD and retaining the retentate;
(e) substituting urea for said guanidine in said retentate by continuing the ultrafiltration step employing an ultrafiltration membrane having a nominal MWCO of approximately 10 kD while replacing guanidine lost in the filtrate with makeup urea to obtain an urea extract solution;
(f) adding NaCl to said urea extract solution to obtain a NaCl concentration of less than about 0.135M and loading said urea extract solution onto a positive anion exchange resin having quaternary amine functional groups;
(g) eluting proteins from said positive anion exchange resin with a first eluant having a NaCl concentration of between about 0.23M and about 0.27M to obtain an anion exchanged fraction eluate;
(h) adjusting the pH of said anion exchanged fraction eluate to about pH 4.8;
(i) adding NaCl to said anion exchanged fraction eluate to obtain a NaCl concentration in a range from about 0.23M to about 0.27M and loading said anion exchanged fraction eluate onto a negative cation exchange resin having sulfonic acid functional groups;
(j) eluting proteins from said negative cation exchange resin with a second eluant having a NaCl concentration of between about 0.6M and about 1.5M to obtain a cation exchanged fraction eluate;
(k) dialyzing said cation exchanged fraction eluate to remove low molecular weight species;
(l) loading a second solution comprising proteins from said dialyzed cation exchanged fraction onto a reverse phase HPLC column comprising hydrocarbon-modified silica packing material; and
(m) eluting proteins from said HPLC column with a third eluant, wherein said third eluant has a pH of less than about pH 2, a varying acetonitrile concentration increasing from about 33 percent by volume to about 37 percent by volume and a trifluoracetic acid concentration of between about 0.05 percent by volume and about 0.15 percent by volume.

31. A process, as claimed in claim 20, wherein said anion exchange resin comprises quaternary amine functional groups.

32. A process, as claimed in claim 30, wherein said cation exchange resin comprises sulfonic acid functional groups.

33. A process, as claimed in claim 30, wherein said first solution, said anion exchanged fraction eluate and said cation exchanged fraction eluate each comprise an effective amount of urea to maintain proteins therein in solution.

34. A process, as claimed in claim 30, wherein an osteoinductive factor is produced having, upon hydrolysis, an amino acid composition of from about 20.7 to about 26.1 mole percent ASP(+ASN) and GLU(+GLN); from about 11.3 to about 15.7 mole percent SER and THR; from about 37.6 to about 42.4 mole percent ALA, GLY, PRO, MET, VAL, ILE, and LEU; from about 5.8 to about 7.9 mole percent TYR and PHE; and from about 13.3 to about 19.9 mole percent HIS, ARG, and LYS, based on the total moles of said ASP(+ASN), GLU(+GLN), SER, THR, ALA, GLY, PRO, MET, VAL, ILE, LEU, TYR, PHE, HIS, ARG, and LYS amino acids.

35. A process, as claimed in claim 30, wherein a mixture of proteins is produced which, when subjected to sodium dodecyl sulfate polyacrylamide gel electrophoresis, results in a reduced or non-reduced gel profile comprising substantially all of the protein bands as shown in FIG. 1.

* * * * *